United States Patent [19]

Chamberlain et al.

[11] Patent Number: 5,605,991
[45] Date of Patent: Feb. 25, 1997

[54] MULTIFUNCTIONAL INITIATOR FROM DIVINYL DISLANE

[75] Inventors: Linda R. Chamberlain, Richmond; Ronald J. Hoxmeier; Philip A. DeFriend, both of Houston, all of Tex.

[73] Assignee: Shell Oil Company, Houston, Tex.

[21] Appl. No.: 620,112

[22] Filed: Mar. 21, 1996

[51] Int. Cl.$^6$ .................. C08F 4/48; C07F 7/08
[52] U.S. Cl. ............. 526/178; 526/180; 526/181; 526/340.2; 525/272; 525/308; 525/310; 525/333.1; 525/333.2; 525/333.3; 525/385; 502/155; 502/156; 502/157; 556/431; 556/435; 260/665 R
[58] Field of Search ............ 526/178, 173, 526/180, 181; 502/155, 156, 157; 556/431, 435; 260/665 R; 525/272, 308, 310, 333.1, 333.2, 333.3, 385

[56] References Cited

U.S. PATENT DOCUMENTS

| | | | |
|---|---|---|---|
| 3,383,377 | 5/1968 | Uraneck et al. | 260/94.7 |
| 3,485,857 | 12/1969 | Speier | 260/429 |
| 3,555,066 | 1/1971 | Le Grow | 526/178 X |
| 3,624,057 | 11/1971 | Farrar | 260/83.7 |
| 3,637,899 | 1/1972 | Sergoevich et al. | 260/827 |
| 3,784,637 | 1/1974 | Farrar | 260/448.2 |
| 3,959,412 | 5/1976 | Oberlin | 260/880 |
| 4,145,498 | 3/1979 | Farrar | 526/178 |
| 4,278,774 | 7/1981 | Nametkin et al. | 525/100 |
| 4,704,438 | 11/1987 | Niwa et al. | 525/333.3 |
| 4,843,120 | 7/1989 | Halasa et al. | 525/53 |

FOREIGN PATENT DOCUMENTS

| | | | |
|---|---|---|---|
| 816777 | 6/1973 | Belgium. | |
| 6122387 | 9/1981 | Japan | 556/431 |
| J63278912-A | 5/1987 | Japan. | |
| 4149185 | 5/1992 | Japan | 556/431 |
| 4352790 | 12/1992 | Japan | 556/431 |
| 1256472 | 12/1971 | United Kingdom. | |

OTHER PUBLICATIONS

Auner, N, "Reaktionen Methyl–und Trimethylsubstituierter Vinylsilane–bzw. –Disilane mit LiBu"', *J. of Organometallic Chem.*, 336 (1987) 59–81.

Oku, J. et al., "Anionic Polymerization of Vinylsilanes II. Mechanism of Isomerization in the Polymerization of Trimethylvinylsilane with Butyllithium–$N,N,N'$, $N'$–tetramethylethylenediamine", *Polymer J.*, vol. 23, No. 3, pp. 195–199 (1991).

Primary Examiner—Fred M. Teskin

[57] ABSTRACT

A multifunctional initiator is prepared by contacting an organo-alkali metal compound with a silane represented by the formula:

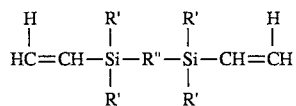

wherein the R' are generally lower alkyl groups such as methyl and the R" is generally an $-(CH_2)_n$ group with n=2. Superior results are obtained presumably because of the separation of the vinyl groups and the greater solubility of the compound because of the R' groups. The resulting catalyst initiates polymerization of monomers such as conjugated dienes and monovinyl substituted aromatic compounds to give relatively monodispersed polymers with little or no crosslinking.

20 Claims, No Drawings

MULTIFUNCTIONAL INITIATOR FROM DIVINYL DISLANE

BACKGROUND OF THE INVENTION

This invention relates to multifunctional organo-alkali metal polymerization initiators. Organo-alkali metal compounds have long been used as anionic polymerization initiators. Such initiators first produce what is known in the art as a living polymer. There are three basic methods of carrying out such polymerizations.

In the first, a monomer or a sequence of monomers is simply combined with a monofunctional initiator such as secondary butyllithium and after the desired chain length is achieved the initiator is terminated. In the second, the monomer or a sequence of monomers is contacted with a monofunctional initiator, generally secondary butyllithium, and polymerization is carried out until chains of about ½ the desired length are produced after which a difunctional coupling agent is introduced. Alternatively, chains can be ⅓ of the desired length in a trifunctional coupling agent utilized, etc. These processes both give excellent results in commercial scale operations. However, there are times when it would be desirable to have a polymer with a functional group on each end of the polymer chain. With the first process just described, the active lithium entity is only at one end of the growing chain. In the second method just described, the active lithium entities are positioned in the middle of the coupled polymers.

The third method utilizes a multifunctional organolithium initiator such as the diadduct produced by reacting secondary butyllithium with divinylbenzene or substituted divinylbenzenes. These initiators, by virtue of having an active lithium atom at each end grow more or less symmetrically. When the chain reaches the desired lengths, there is an active lithium at each end which can be reacted with the appropriate materials to give functional groups such as OH on each end. This solves the problem of not having an alkali metal atom at each end, but creates new problems. For one thing, the initiators frequently are not soluble in the polymerization solvent. Also the living polymer chain ends seem to associate with each other which causes the polymer to gel as soon as the reaction starts.

It was long ago proposed to prepare multifunctional lithium initiators by reacting an organolithium compound with a polyvinyl silane. While such systems are operable, they give erratic results. For one thing the measured molecular weight tends to be far below the calculated molecular weight indicating that a major amount of the initiator is effectively monofunctional. Also because of the erratic polymerization, there is no uniformity of chain length and thus, an undesirably broad molecular weight distribution results. Finally, as noted hereinabove, the ends of the living chain seem to associate which can result in crosslinking thus giving polymers having higher molecular weight then the target value.

SUMMARY OF THE INVENTION

It is an object of this invention to provide an improved multifunctional organo-alkali metal initiator;

It is a further object of this invention to provide a process for producing multifunctional initiators capable of giving narrow molecular weight distribution;

It is yet a further object of this invention to avoid catalyst solubility problems; and It is still yet a further object of this invention to provide an improved polymerization process utilizing a multifunctional initiator.

In accordance with this invention, a divinyl disilyl compound is reacted with an organo-alkali metal compound in the presence of an ether or amine promoter to give a multifunctional initiator.

DETAILED DESCRIPTION OF THE INVENTION

It has been found that by using a divinylsilane with more than one silicon, in combination with an ether or amine promoter, a difunctional initiator can be produced which avoids the problems of erratic polymerization behavior.

The reaction to produce this initiator can be depicted as follows:

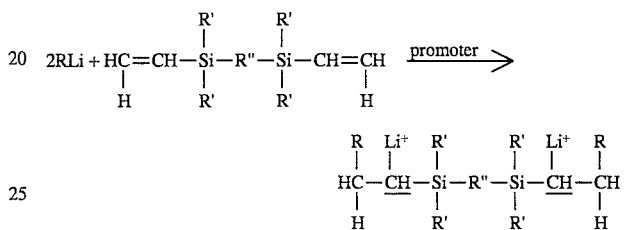

In the monofunctional organo alkali metal compound, the R is a 1 to 20 carbon atom alkyl or cycloalkyl or a 6 to 10 carbon atom aryl. The alkali metal is preferably lithium as depicted in the formula. The preferred material is secondary butyllithium. Exemplary of other suitable organolithium compounds are ethyllithium, n-propyllithium, isopropyllithium, n-butyllithium, tert-butyllithium, tert-octyllithium, n-decyllithium, n-eicosyllithium, phenyllithium, 2-naphthyllithium, 4-butylphenyllithium, 4-tolyllithium, 4-phenyllithium, cyclohexyllithium, 3,5-di-n-heptylcyclohexyllithium, and 4-cyclopentylbutyllithium.

In the divinyl disilane compound, each R' is individually selected from 1 to 20 carbon atom alkyl groups, 6 to 10 carbon atoms aryl groups and hydrogen with the provision that no more than two of the R' groups are hydrogen and no more than one H is on either Si. Preferably none of the R' groups are hydrogen since the R groups enhance the solubility of the resulting catalyst in the solvent. However, depending on the solvent in question and the length of the carbon chains of the other R' groups, one or two of the R' groups could be hydrogen. Preferably, the R' groups are 1 to 4, more preferably 1 carbon atom alkyl, i.e. methyl.

R" is an $-(CH_2)_n-$ moiety where n=1 to 20, preferably 2 to 8 and most preferably, n=2. As used herein $-(CH_2)_n-$ includes branched analogs.

The reaction must be carried out in the presence of a promoter which can be an ether or an amine. Preferably a chelating ether or amine, is utilized. By chelating ether is meant an ether having more than one oxygen as exemplified by the formula $R'''(OR'''')_m(OR''')_n$ where each R''' is individually selected from 1 to 8, preferably 2 to 3 carbon atom alkyl radicals and R'' is a 1 to 6, preferably 2 to 3 carbon atom alkylene radical and m and n are independently selected integers of 1–3, preferably 1–2. Examples of preferred ethers include 1,2-diethoxyethane and 1,2-dimethoxyethane (glyme). Other suitable materials include $CH_3-OCH_2-CH_2-OCH_2-CH_2-OCH_3$ (diglyme) and $CH_3-CH_2-OCH_2-CH_2-OCH_2-CH_2-OCH_2-CH_3$.

By chelating amine is meant an amine having more than one

N such as N,N,N',N'-tetramethylethylene diamine as opposed to a monoamine such as triethylamine. The monoamines are operable but less preferred. Less preferred also are straight chain and cyclic monoethers such as dimethylether, diethylether, anisole, and tetrahydrofuran.

The promoter is used in an amount of at least 0.05 moles per mole of lithium compound, preferably 0.01–20, and most preferably 0.4–10 moles of promoter per mole of the lithium compound. Within the most preferred range, which is quite broad both target MWs vs actual MWs and polydispersity were excellent.

This reaction could be carried out in a diluent or solvent and the product recovered. However, it is much preferred to carry out the reaction in the polymerization zone utilizing the solvent which will be utilized in the polymerization itself. Hence, relative to the solvent the amount of promoter is relatively small, i.e. 10 parts per million to about 1%, preferably 100 parts per million to 10,000 parts per million, most preferably 500 parts per million to 2000 parts per million. This can vary widely, however, since extremely small amounts are effective to bring about some improvement. The upper end of the range is limited by the economics of the cost of the material and the adverse effect extremely large quantities would have on the subsequent polymerization in the preferred instances where the reaction is carried out in the presence of the polymerization solvent. In the less preferred embodiment where the reaction is not carried out in the presence of the actual polymerization solvent, the promoter could constitute the solvent for the reaction but this would be decidedly less preferred.

The organo-alkali metal compound and the silane are preferably used in about stoichiometric amounts, i.e. 2 moles of the alkali metal compound per mole of silane, i.e. a 1:1 equivalent basis. Some leeway is possible, however, and the organic alkali metal compound can be utilized in an amount within the range of 1 to 3 equivalents per equivalent of the silane.

While the examples were carried out utilizing the 1 hour reaction time, in fact the reaction is essentially instantaneous. Consequently, the reaction time can vary from as little as a few seconds to a few hours, generally 10 seconds to 1 hour and can be carried out on either a continuous or batch process. Reaction can be carried out at any convenient temperature with room temperature being suitable. More broadly temperatures of 15° to 150° C., preferably 20° to 90° C. are suitable since in the preferred embodiment the initiator is produced in situ in the polymerization zone, the temperature can be that subsequently to be used for the polymerization, generally 15° to 150° C., preferably 40° to 90° C. Alternatively, the reaction can be carried out at a different temperature and the temperature adjusted to the optimum polymerization temperature after contact between the organo-alkali metal and the divinyldisilane.

The subsequent polymerization would generally be carried out for a time within the range of 1 minute to 6 hours, preferably 10 minutes to 4 hours, more preferably 10 minutes 2 hours.

If the formation of the initiator and/or the polymerization is carried out at a temperature above the boiling point of the reaction mixture, then reflux and/or elevated pressure can be used to maintain liquid conditions in the reaction medium.

At the conclusion of the polymerization, polymer can be recovered using any conventional technique. For instance, it can be simply terminated through the addition of a chain transfer agent such as carbon monoxide, oxygen, alcohol, or other known terminating agents such as acetone or acetaldehyde to deactivate the organo-alkali metal "living polymer" and allow recovery of the finished polymer.

However, the principle object of this invention is to utilize the presence of the organo-alkali metal on each end of the polymer chain. Consequently a functional group can be incorporated onto each end of the polymer chains. For instance, the polymer can be treated with ethylene oxide to give, in the case of lithium as organo-alkali metal, —OLi at the ends of the polymer chains followed by the addition of an alcohol to give —OH terminal groups. Thus a diol polymer is produced, i.e. one with an OH at each end of the polymer chain which can be of value for various further reactions. U.S. Pat. No. 5,166,277, the disclosure of which is hereby incorporated by reference discloses termination with ethylene oxide.

Electrophiles such as isocyanates, halides or halo silanes may be added to produce amides, halides or halo silane functionality at each end of the polymer chains. Alternatively, the polymer chains can be endcapped with materials such as 1-4-formylmethylbenzoate, 4-formylbenzocyclobutane, t-dimethylamino-benzaldedehyde or epoxy ketones.

The amount of the organo-alkali metal initiator employed depends upon the desired properties of the polymer, particularly the desired molecular weight. Normally, the organo-alkali metal initiator is employed in the range of 0.1 to 100 moles per 100 grams of total monomers, although larger or smaller amounts can be used if very low or very high molecular weight polymer is desired.

The catalyst of this invention can be used to polymerize monomers to give homopolymers, block copolymers or random copolymers. Suitable monomers include conjugated alkadienes and monoalkenyl aromatic hydrocarbons. The conjugated alkadiene preferably have 4 to 8 carbon atoms per molecule. Illustrative of such conjugated alkadienes are 1,3-butadiene (butadiene), 2-methyl-1,3-butadiene (isoprene), 1,3-pentadiene (piperylene), 1,3-octadiene, and 2-methyl-1,3-pentadiene. Preferred conjugated alkadienes are butadiene and isoprene. The preferred monoalkenyl aromatic compounds have 8 to 20 carbon atoms per molecule with alkenyl groups of up to 3 carbon atoms attached to a benzene ring as exemplified by styrene and styrene homologs such as $\alpha$-methylstyrene and paramethylstyrene. Styrene and $\alpha$-methylstyrene are particularly preferred monoalkenyl aromatic compounds, especially styrene.

Mixtures of the above described monomers can be utilized. One particularly suitable mixture is a mixture of a conjugated alkadiene such as butadiene or isoprene with a monoalkenyl aromatic compound such as styrene. Both elastomeric and resinous polymer can be produced depending on whether a conjugated alkadiene or a monoalkenyl aromatic compound is used as the monomer. Mixtures of 50–99 wt % conjugated alkadiene and 1–50 wt % monoalkenyl aromatic compound also can be used to produce elastomeric materials. Again the preferred examples of this would be butadiene and styrene or isoprene and styrene.

EXAMPLES

Run 1—Control-Monosilane

Under an inert nitrogen atmosphere (dribox), 200 grams of alumina treated cyclohexane was added to a 500 ml round bottom flask with stirring bar. 1000 ppm (based on cyclohexane) i.e. 0.20 grams of glyme was added to the cyclohexane solution. Then to the stirring solution, 4.13 grams of a 10.89% concentration of a s-butyllithium in cyclohexane (7 mmoles) and 0.396 grams (3.53 mmoles) of divinyldimethylsilane was added. The solution was allowed to stir at 25° C. for one hour. After one hour of stirring, 35.24 grams of alumina treated isoprene monomer was added. The target polyisoprene molecular weight was 10,000. The solution had a light yellow color which gradually became an intense yellow color during the 72 hour reaction. Also, no precipitates were observed. To terminate the isoprene polymerization, 3 mls of methanol was added to the polymeric solution. The solvent was vacuum removed leaving a clear polymeric material. According to GPC results, the corrected molecular weight of the polyisoprene was 19,865 with a polydispersity of 1.44.

Run 2—Control-Monosilane

Under an inert nitrogen atmosphere (dribox), 90 grams of alumina treated cyclohexane was added to a 250 ml round bottom flask with stirring bar. 1000 ppm (based on cyclohexane) i.e. 0.09 grams of glyme was added to the cyclohexane solution. Then to the stirring solution, 1.06 grams of a 12.11% concentration of s-butyllithium in cyclohexane and 0.11 grams (0.98 mmoles) of divinyldimethylsilane was added. The solution was allowed to stir at 25° C. for one hour. After one hour of stirring, 10.0 grams of alumina treated isoprene monomer was added. The target polyisoprene molecular weight was 10,000. The solution had a light yellow color which gradually became an intense yellow color during the 1 hour reaction. Also, no precipitates were observed. To terminate the isoprene polymerization, 3 mls of methanol was added to the polymeric solution. The solvent was vacuum removed leaving a clear polymeric material. According to GPC results, the corrected molecular weight of the polyisoprene was 16,440 with a polydispersity of 1.92.

Run 3—Control—No Promoter

Under an inert nitrogen atmosphere (dribox), 200 grams of alumina treated cyclohexane was added to a 500 ml round bottom flask with stirring bar. Glyme was not added to the cyclohexane solution. Then to the stirring solution 3.96 grams of a 12.11% concentration of s-butyllithium in cyclohexane and 0.74 grams (3.75 mm) of 1,4 divinyl, 1,1,4,4, tetramethyldisilylethylene were added. The solution was allowed to stir at 25° C. for one hour. After one hour of stirring, 30.00 grams of alumina treated isoprene was added. The target polyisoprene molecular weight was 8,000. The solution was allowed to stir for 1 hour at 25° C. The solution had a light yellow color which gradually became an intense yellow color during the 1 hour reaction. Also, no precipitates were observed. To terminate the isoprene polymerization, 3 mls of methanol were added to the polymeric solution. The solvent was vacuum removed leaving a clear polymeric material. According to GPC results, the corrected molecular weight of the polyisoprene was 4,795 with a polydispersity of 1.52.

Run 4—Invention

Under an inert nitrogen atmosphere (dribox), 150 grams of alumina treated cyclohexane was added to a 500 ml round bottom flask with stirring bar. 1000 ppm (based on cyclohexane) i.e. 0.15 grams of glyme was added to the cyclohexane solution. Then to the stirring solution, 21.14 grams of 12.11% concentration of s-butyllithium in cyclohexane and 3,96 grams (20.0 mm) of 1,4 divinyl-1,1,4,4, tetramethyldisilylethylene was added. The target polyisoprene molecular weight was 1500. The solution was allowed to stir for 1 hour at 25° C. The solution had a light yellow color which gradually became an intense yellow color during the 1 hour reaction. Also, no precipitates were observed. To terminate the isoprene polymerization, 3 mls of methanol was added to the polymeric solution. The solvent was vacuum removed leaving a clear polymeric material. According to GPC results, the corrected molecular weight of the polyisoprene was 2055 with a polydispersity of 1.34. Carbon 13 NMR data showed a molecular weight of 1653 and silicone present in the polyisoprene backbone.

Run 5—Invention

Under an inert nitrogen atmosphere (dribox), 200 grams of alumina treated cyclohexane was added to a 500 ml round bottom flask with stirring bar. 1000 ppm (based on total solution) i.e. 0.24 grams of glyme was added to the cyclohexane solution. Then to the stirring solution, 4.13 grams of a 10.89% concentration of s-butyllithium in cyclohexane and 0.70 grams (3.529 mm) of 1,4 divinyl, 1,1,4,4, tetramethyldisilylethylene were added. The solution was allowed to stir at 25° C. for one hour. After one hour of stirring, 35.29 grams of alumina treated isoprene was added. The target polyisoprene molecular weight was 10,000. The solution was allowed to stir for 4 hours at 25° C. The solution had a light yellow color which gradually became an intense yellow color during the 4 hour reaction. Also, no precipitates were observed. To terminate the isoprene polymerization, 3 mls of methanol were added to the polymeric solution. The solvent was vacuum removed leaving a clear polymeric material. According to GPC results, the corrected molecular weight of the polyisoprene was 10,960 with a polydispersity of 1.23. Carbon 13 NMR data showed a molecular weight of 9600 and silicone present in the polyisoprene backbone.

Run 6 and 7—Invention

Under an inert nitrogen atmosphere (dribox), 90 grams of alumina treated cyclohexane was added to a 250 ml round bottom flask (Flask A) with stirring bar. 1000 ppm (based on cyclohexane) i.e. 0.09 grams of glyme was added to the cyclohexane solution. Then to the stirring solution, 1.06 grams of a 12.11% concentration of s-butyllithium in cyclohexane and 0.20 (1.0 mm) of 1,4 divinyl 1,1,4,4 tetramethyldisilylethylene was added. The solution was allowed to stir at 25° C. for one hour. After one hour of stirring, 10.0 grams of alumina treated isoprene monomer was added. The target polyisoprene molecular weight was 10,000. The solution had a light yellow color which gradually became an intense yellow color during the 1 hour reaction. Also, no precipitates were observed. After polymerization, ½ of the living polyisoprene solution was dispensed into another 250 mol round bottom flask with stirring bar (Flask B). To terminate the isoprene polymerization in Flask A, 0.28 grams (4.28 mm) of oxetane (propylene oxide) was added. To terminate the isoprene polymerization in Flask B, 0.28 grams of t-butylmethacrylate (1.96 mm) was added. Each polyisoprene solution was allowed to stir for 10 minutes. The solvent was vacuum removed leaving a clear polymeric material in each flask. According to GPC results, the corrected molecular weight of polyisoprene in Flask A was 14,385 with a polydispersity of 1.19. The corrected molecular weight of the polyisoprene in Flask B was 14,385 with a polydispersity of 1.26 and with 26.4% coupled material with a corrected molecular weight of 28,770. Infra red analysis of the polymer in Flask A showed a signal at 3488 $cm^{-1}$, indicative of incorporation of —OH endgroups from the oxetane terminating step. Infra red analysis of the polymer in Flask B showed a signal at 1726 cm$^{-1}$, indicative of incorporation of tert-butyl methacrylate endgroups from the tert-butyl methacrylate terminating step.

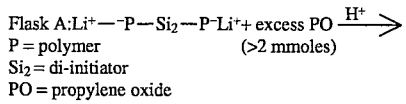

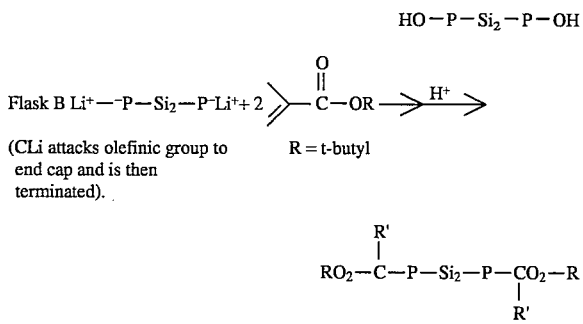

The use of R and R' in this example is meant to apply only to this example since these terms have been used in another context in other places in this application.

Run 9—Invention

Under an inert nitrogen atmosphere (dribox), 90 grams of alumina treated cyclohexane was added to a 250 ml round bottom flask with stirring bar. 1000 ppm (based on cyclohexane) or 0.09 grams of glyme was added to the cyclohexane solution. Then to the stirring solution, 0.21 grams of a 12.11% concentration of s-butyllithium in cyclohexane and 0.04 (0.02 mm) of 1,4 divinyl-1,1,4,4 tetramethyldisilylethylene was added. The solution was allowed to stir at 25° C. for one hour. After one hour of stirring, 10. grams of alumina treated isoprene monomer was added. The target polyisoprene molecular weight was 50,000. The solution had a light yellow color which gradually became an intense yellow color during the 1 hour reaction. Also, no precipitates were observed. To terminate the isoprene polymerization, 3 mls of methanol was added to the polymeric solution. The solvent was vacuum removed leaving a clear polymeric material. According to GPC results, the corrected molecular weight of the polyisoprene was 34,250 with a polydispersity of 1.11.

The results of these nine runs are summarized in the following table.

TABLE

ISOPRENE POLYMERIZATION WITH DIFUNCTIONAL INITIATORS

| | Initiator Preparation | | | | | Polymerization | | | |
|---|---|---|---|---|---|---|---|---|---|
| Run | Glyme[1] (gms.) | Silane[2] | S-Buli (gms.) | Glyme: S-Buli[3] | Glyme: Solvent | Poly (hrs.) | Target (mw.) | Corr. MW (m. peak)[4] | MW Dispersity |
| 1 | 0.24 | Mono | 0.45 | 0.38 | 0.001 | 72 | 10K | 19.865K | 1.44 |
| 2 | 0.09 | Mono | 0.13 | 0.49 | 0.001 | 1 | 10K | 16.44K | 1.92 |
| 3 | — | Di | 0.48 | — | — | 1 | 8.0K | 4.795K | 1.52 |
| 4 | 0.15 | Di | 2.56 | 0.042 | 0.001 | 1 | 1.5K | 2.055K | 1.3K |
| 5 | 0.24 | Di | 0.45 | 0.38 | 0.001 | 4 | 10K | 10.96K | 1.23 |
| 6 | 0.045 | Di | 0.064 | 0.50 | 0.001 | 1 | 10K | 14.39K | 1.19 |
| 7 | 0.045 | Di | 0.064 | 0.50 | 0.001 | 1 | 10K | 14.39K | 1.26 |
| 8 | 0.09 | Di | 0.0097 | 6.60 | 0.001 | 1 | 50K | 62.3K | 1.18 |
| 9 | 0.09 | Di | 0.0048 | 13.33 | 0.001 | 1 | 50K | 34.3K | 1.11 |

[1]CH$_3$OCH$_2$CH$_2$OCH$_3$
[2]Mono is prior art divinyldimethylsilane; Di is 1,4 divinyl, 1,1,4,4, tetramethyldisilylethylene
[3]Moles/mole butyllithium
[4]Molecular weights of linear polydienes are conveniently measured by gel permeation chromatography (GPC) where the GPC system has been appropriately calibrated.

Run 8—Invention

Under an inert nitrogen atmosphere (dribox), 90 grams of alumina treated cyclohexane was added to a 250 ml round bottom flask with stirring bar. 1000 ppm (based on cyclohexane) i.e. 0.09 grams of glyme was added to the cyclohexane solution. Then to to stirring solution, 0.21 grams of a 12.11% concentration of s-butyllithium in cyclohexane and 0.08 (0.4 mm) of 1,4 divinyl-1,1,4,4, tetramethyldisilylethylene was added. The solution was allowed to stir at 25° C. for one hour. After one hour of stirring, 10.0 grams of alumina treated isoprene monomer was added. The target polyisoprene molecular weight was 50,000. The solution had a light yellow color which gradually became an intense yellow color during the 1 hour reaction. Also, no precipitates were observed. To terminate the isoprene polymerization 3 mls of methanol was added to the polymeric solution. The solvent was vacuum removed leaving a clear polymeric material. According to GPC results, the corrected molecular weight of the polyisoprene was 62,335 with a polydispersity of 1.18.

Molecular weights of linear polydienes are conveniently measured by Gel Permeation Chromatography (GPC), where the GPC system has been appropriately calibrated. Polymers of known molecular weight are used to calibrate and these must be of the same molecular structure and chemical composition as the unknown linear polymers or segments that are to be measured. For anionically polymerized linear polymers, the polymer is essentially monodispersed and it is both convenient and adequately descriptive to report the "peak" molecular weight of the narrow molecular weight distribution observed. In some runs this was confirmed with carbon 13 NMR data.

As control Run 1 shows, prior art monosilane initiators exhibit significant deficiencies. For one thing, it took an exorbitantly long time to effect the polymerization. This apparently resulted in crosslinking as evidenced by the molecular weight exceeding the target. In addition the molecular weight dispersity was relatively high. The molecular weight dispersity is a measure of the breadth of the molecular weight distribution with a uniform distribution being evidenced by a dispersity of 1.00. More specifically, this is determined by Gel Permeation Chromatography. Run 2 shows that once again prior art monosilane gave high dispersity and failed to meet the target molecular weight because of crosslinking. Run 3 shows the effect of utilizing the novel dilithium initiator of this invention without a promoter. As can be seen it failed to produce a diinitiator and also gave relatively broad molecular weight distribution. Invention Runs 4 through 9 show under a variety of conditions, polymers produced with relatively narrow molecular weight distribution. In addition, the molecular weight achieved in all instances was reasonably close to the target molecular weight indicating the actual production of a diinitiator and the absence of substantial amounts of crosslinking.

While this invention has been described in detail for the purpose of illustration, it is not to be construed as limited thereby, but is intended to cover all changes and modifications within the spirit and scope thereof.

We claim:

1. A process for forming a multifunctional initiator in a reaction zone comprising:

contacting an organo-alkali metal compound with a silane represented by the formula

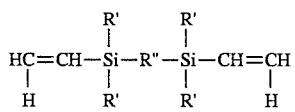

wherein each R' is individually selected from the group consisting of 1–20 carbon atom alkyl groups, 6–10 carbon atom aryl groups and H with the provision that no more than two of the R' groups are H, and no more than 1 H is on either Si;

wherein R" is an $-(CH_2)_n-$ moiety where n=1 to 20;

wherein said contacting is carried out in the presence of a promoter selected from the group consisting of ethers and amines, said promoter being present in an amount of at least 0.1 moles per mole of said organo-alkali metal compound.

2. A method according to claim 1 wherein said organo-alkali metal compound is an alkyllithium compound, all of said R' groups are 1–4 carbon atom alkyl groups, R" is an $-(CH_2)_n-$ moiety where n=2 to 8, and wherein said contacting is carried out in a hydrocarbon solvent.

3. A method according to claim 2 wherein said hydrocarbon solvent is cyclohexane.

4. A method according to claim 2 wherein said alkyllithium is secondary butyllithium.

5. A method according to claim 2 wherein said silane is 1,4-divinyl-1,1,4,4-tetramethyldisilylethylene.

6. A method according to claim 2 wherein said promoter is an ether.

7. A method according to claim 2 wherein said promoter is an ether of the formula R'''('OR'''')$_m$(OR''')$_n$ wherein each R''' is individually selected from 1 to 8 carbon atom alkyl radicals, R'''' is a 1–6 carbon atom alkylene radical and m and n are independently selected integers of 1–3.

8. A method according to claim 2 wherein said ether is selected from the group consisting of 1,2-diethoxyethane and 1,2-dimethoxyethane.

9. A method according to claim 2 wherein said ether is 1,2-dimethoxyethane and said ether is present in an amount within the range of 0.01–20 moles per mole of said alkyllithium.

10. The method according to claim 2 wherein said promoter is present in an amount within the range of 0.04–10 moles per mole of said alkyllithium.

11. A method according to claim 2 wherein said reaction zone is a polymerization zone and wherein said hydrocarbon solvent is polymerization solvent and wherein after said contacting, at least one monomer is introduced and polymerization carried out.

12. A method according to claim 11 wherein said at least one monomer is selected from the group consisting of butadiene, isoprene, styrene and mixtures thereof, to give homopolymers, block copolymers or random copolymers.

13. A method according to claim 12 wherein said monomer is isoprene.

14. A method comprising contacting secondary butyllithium with 1,4-divinyl-1,1,4,4-tetramethyldisilylethylene in a cyclohexane polymerization solvent in the presence of 0.04–10 moles of 1,2-dimethoxyethane per mole of said secondary butyllithium to produce a multifunctional initiator in situ, thereafter introducing a monomer selected from the group consisting of isoprene, butadiene and styrene into said polymerization zone to give a polymerization mixture and maintaining said polymerization mixture under polymerization conditions for a time sufficient to give a polymer.

15. A method according to claim 14 wherein said contacting is carried out at about room temperature for a time within the range of 10 seconds to 1 hour and wherein said polymerization conditions include a temperature within the range of 40°–90° C. and a time within the range of 10 minutes to 4 hours.

16. A method according to claim 15 wherein said polymer is contacted with ethylene oxide prior to said recovery so as to give a polydiol polymer.

17. A method according to claim 15 wherein said polymer is contacted with propylene oxide prior to said recovery so as to give a polydiol polymer.

18. A method according to claim 15 wherein said polymer is contacted with t-butyl methacrylate prior to said recovery to give t-butyl methacrylate end groups.

19. A composition represented by the formula

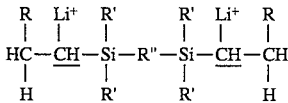

wherein each R is selected from the group consisting of 1–20 carbon atom alkyl groups, 1–20 carbon atoms cycloalkyl groups, and 6–10 carbon atoms aryl groups;

each R' is individually selected from the group consisting of 1–20 carbon atom alkyl groups, 6–10 carbon atom aryl groups and H with the provision that no more than 2 of the R' groups are H; and no more than one H group is on either Si; and wherein R" is an $-(CH_2)_n-$ moiety where n=1 to 20.

20. A composition according to claim 19 wherein each R is secondary butyl, each R' is methyl and n=2.

* * * * *